(12) United States Patent
Pirot et al.

(10) Patent No.: US 9,233,079 B2
(45) Date of Patent: Jan. 12, 2016

(54) METHOD FOR PRODUCING NANOCAPSULES IN THE ABSENCE OF AN ORGANIC SOLVENT, AND NANOCAPSULES PRODUCED THEREBY

(71) Applicant: UNIVERSITE CLAUDE BERNARD LYON I, Villeurbanne (FR)

(72) Inventors: Fabrice Pirot, Lyons (FR); Francoise Falson, La Tour de Salvagny (FR)

(73) Assignee: UNIVERSITE CLAUDE BERNARD LYON I, Villeurbanne (FR)

(*) Notice: Subject to any disclaimer, the term of this patent is extended or adjusted under 35 U.S.C. 154(b) by 84 days.

(21) Appl. No.: 13/757,342

(22) Filed: Feb. 1, 2013

(65) Prior Publication Data
US 2013/0207286 A1 Aug. 15, 2013

Related U.S. Application Data

(62) Division of application No. 12/988,380, filed as application No. PCT/FR2009/050680 on Apr. 14, 2009, now abandoned.

(30) Foreign Application Priority Data

Apr. 18, 2008 (FR) ..................................... 08 52648

(51) Int. Cl.
*B01J 13/10* (2006.01)
*A61K 9/51* (2006.01)

(52) U.S. Cl.
CPC ............... *A61K 9/5192* (2013.01); *B01J 13/10* (2013.01)

(58) Field of Classification Search
None
See application file for complete search history.

(56) References Cited

U.S. PATENT DOCUMENTS

| 6,884,438 B1 | 4/2005 | Quintanar et al. |
| 2003/0224060 A1 | 12/2003 | Simonnet et al. |
| 2005/0175651 A1* | 8/2005 | Simonnet et al. ............. 424/401 |
| 2007/0134332 A1* | 6/2007 | Turnell et al. ................. 424/486 |

FOREIGN PATENT DOCUMENTS

| FR | 2 766 368 | | 1/1999 | |
| FR | WO 9904766 | * | 2/1999 | ............... A61K 9/51 |

OTHER PUBLICATIONS

Reis et al. (Nanomedicine: Nanotechnology, Biology, and Medicine 2006;2:8-21).*

(Continued)

*Primary Examiner* — Ernst V Arnold
(74) *Attorney, Agent, or Firm* — Clark & Brody

(57) ABSTRACT

A method for preparing an aqueous suspension of nanocapsules comprising an oily core surrounded by a polymeric shell, comprises mixing first and second phases, wherein the first oily phase comprises a hydrophobic polymer, an oil or a mixture of oils, at least one active ingredient, and a surfactant $TA_1$. The oily phase is brought to a temperature $T_1$ higher than the melting point of the hydrophobic polymer, the hydrophobic polymer being miscible, at this temperature $T_1$, with the mixture of the surfactant $TA_1$ and the oil or mixture of oils, and the active ingredient being miscible, soluble or solubilized in the mixture of the surfactant $TA_1$ and the oil or mixture of oils. The second polar phase comprises a hydrophilic polymer in the form of a hydrogel in an aqueous solution containing a surfactant $TA_2$, to form the nanocapsules in an aqueous suspension.

20 Claims, 1 Drawing Sheet

(56) References Cited

OTHER PUBLICATIONS

Green et al. (Quality Assurance of Polymeric Materials and Products 1983; issue 846; ASTM International; p. 54).*
Meier (Chem. Soc. Rev., 2000, 29:295-303).*
Benita (Microencapsulation 2005, 2nd Edition CRC Press, p. 218).*
Hassan Lboutounne et al., "Sustained ex vivo . . . as a digluconate", Journal of Controlled Release82 (2002) 319-334.
H. Lboutounne et al., "Characterization of . . . Rat Skin", Skin Pharmacol Physiol 2004; 17: 176-182.
Dang Thi Tuyet Nhung et al., "Sustained antibacterial . . . nanocapsules (Nanochlorex)", International Journal of Pharmaceutics 334, 2007, 166-172.
Jameela, S.R. et al., "Protein release from . . . A comparative study", Journal of Biomaterials Science, Polymer Edition, vol. 8, 1997, pp. 457-466.

Fabiana Quaglia et al., "Nanoscopic core-shell . . . star-diblock copolymers", International Journal of Pharmaceutics 324 (2006), 56-66.
E Mathiowitz et al., "Polyanhydride Microspheres . . . Microencapsulation", Journal of Controlled Release, 5 (1987) 13-22.
H. Fessi et al., "Nanocapsule formation . . . solvent displacement", International Journal of Pharmaceutics, 55 (1989) R1-R4.
Delphine Moinard-Checot et al., "Mechanism of . . . emulsion-diffusion process", Journal of Colloid and Interface Science 317 (2008) 458-468.
I. Limayem Blouza et al., "Preparation and . . . paediatric use", International Journal of Pharmaceutics, 325 (2006) 124-131.
http://www.thefreedictionary.com/colloidal+gel [online] retrieved on Jan. 12, 2013.

* cited by examiner

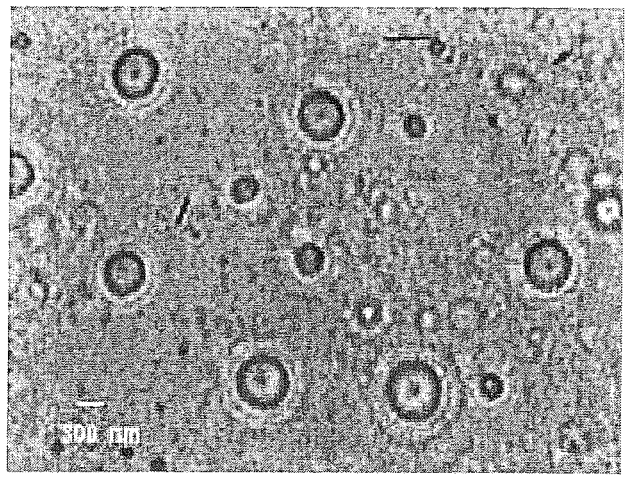

METHOD FOR PRODUCING NANOCAPSULES IN THE ABSENCE OF AN ORGANIC SOLVENT, AND NANOCAPSULES PRODUCED THEREBY

FIELD OF THE INVENTION

The present invention relates to the technical field of nanocapsules, in particular nanocapsules which are of use as agents for transporting an active ingredient.

More specifically, the subject of the invention is a method for producing nanocapsules, and also the nanocapsules which can be obtained by means of such a method.

BACKGROUND ART

Nanoparticles belong to a family of colloidal vectors which can be used, for example, for administering active ingredients, such as therapeutic molecules, in humans or animals. Such colloidal vectors preserve these active ingredients and can enable their controlled and/or sustained release at their site of action. Nanocapsules and nanospheres constitute two distinct groups of nanoparticles. Nanocapsules are formed from an aqueous or oily core coated with a polymeric membrane; nanospheres are formed from a polymeric matrix. The polymers which are part of the composition of nanoparticles are characterized by a high hydrophobicity (e.g. polyesters).

An aqueous suspension of polymeric nanocapsules is most commonly produced according to two techniques:
  by interfacial polymer deposition (H. Fessi, F. Puisieux, J. P. Devissaguet, N. Ammoury, and S. Benita. Nanocapsule formation by interfacial polymer deposition following solvent displacement, *International Journal of Pharmaceutics* 55: R1-R4 (1989));
  by emulsion-diffusion (D. Moinard-Checot, Y. Chevalier, S. Briancon, L. Beney, and H. Fessi. Mechanism of nanocapsules formation by the emulsion-diffusion process. *Journal of Colloid and Interface Science* In Press, Corrected Proof: 77).

These two techniques require the use of organic solvents in order to dissolve the constitutive hydrophobic polymers of the polymeric membrane of the nanocapsules.

The technique of obtaining an aqueous suspension of polymeric nanoparticles by interfacial polymer deposition, which is the most common method for producing nanocapsules, is based on the deposition of preformed polymers at the interface between (i) an organic solvent mixed with an oil and (ii) an aqueous solution. In this process, a solution is prepared containing, e.g., an active ingredient in an organic solvent which is soluble or very soluble in water, such as acetone (with or without lipophilic surfactant). An oil which is miscible in the organic solvent but immiscible in water is added to the previous organic solution. The organic solution is then dispersed, by mechanical stirring, in the polar phase most commonly containing a hydrophilic surfactant (e.g., poloxamer, polysorbate 80). The organic solvent diffuses in the polar phase and this results in aggregation of the polymer around the lipid droplets responsible for the formation of the nanocapsules. The organic solvent can be dispersed in the polar phase by tangential membrane filtration followed by mechanical stirring (I. Limayem Blouza, C. Charcosset, S. Sfar and H. Fessi. Preparation and characterization of spironolacton-loaded nanocapsules for paediatric use *International Journal of Pharmaceutics* 325:124-131(2006)). The organic solvent is removed either by dialysis or, most commonly, by evaporation under reduced pressure.

The emulsion-diffusion technique (D. Moinard-Checot, Y. Chevalier, S. Briancon, L. Beney, and H. Fessi. Mechanism of nanocapsules formation by the emulsion-diffusion process. *Journal of Colloid and Interface Science* In Press, Corrected Proof: 77), for its part, consists in forming an emulsion in which the oily phase contains a biodegradable polymer and a partially water-miscible solvent (e.g., ethyl acetate, solubility: 8.3 g/100 ml at 20° C.) and or the polar phase containing an emulsifier is saturated with ethyl acetate. The addition of water to this emulsion causes diffusion of the solvent of the oil droplets toward the external phase, which leads to precipitation of the polymer around the oil droplets, and therefore the formation of nanocapsules. The organic solvent is removed either by dialysis or, most commonly, by evaporation under reduced pressure.

Consequently, the current methods for producing nanocapsules all comprise a preliminary step of dissolving the hydrophobic polymers in a mixture of one or more volatile organic solvents (e.g., acetone, ethyl acetate). The "spontaneous" formation of the nanocapsules is provided by the dispersion of the organic solutions of hydrophobic polymers in a polar mixture (e.g., most commonly aqueous solutions). The final production step requires evaporation under vacuum or dialysis of the organic solvents. The verification of the elimination of these solvents and the detection of possible traces thereof in the final preparation both constitute procedures which are lengthy and expensive and which require, on the industrial scale, the designing and setting up of complex infrastructures.

SUMMARY OF THE INVENTION

In this context, the present invention proposes to provide a novel method for preparing nanocapsules which is easier to carry out and which is suitable for an industrial scale.

Moreover, one of the essential objectives of the present invention is to provide a method for preparing nanocapsules which are free of toxic products and stable in colloidal suspension, and which allows good protection of the encapsulated active ingredient, along with sustained and/or controlled release of said active ingredient in vivo.

Another essential objective of the present invention is to provide a method for preparing nanocapsules of the abovementioned type and which is also easy to carry out and cost-effective on the industrial scale since it does not require laborious and expensive purification steps.

Another objective of the invention is to provide a method for preparing nanocapsules which makes it possible to reliably and reproducibly obtain nanocapsules having a size of less than 1 μm.

The method according to the invention does not use any organic solvent, which makes it possible to exempt it from the long and expensive steps of eliminating the organic solvent, which are indispensable in the prior art techniques.

In this context, the invention relates to a method for preparing an aqueous suspension of nanocapsules comprising an oily core surrounded by a polymeric shell, in which method the following phases are mixed:
  a) a first phase, called an oily phase, comprising:
  a hydrophobic polymer,
  an oil, or a mixture of oils,
  at least one active ingredient,
  and a surfactant $TA_1$,
  this oily phase being brought to a temperature $T_1$ higher than the melting point of the hydrophobic polymer, the hydrophobic polymer being miscible, at this temperature $T_1$, with the mixture of the surfactant $TA_1$ and the oil or mixture of oils, and the active ingredient being miscible, soluble or solubilized in the mixture of the surfactant $TA_1$ and the oil or mixture of oils;

b) a second phase, called a polar phase, comprising a hydrophilic polymer in the form of a hydrogel in an aqueous solution containing a surfactant $TA_2$, in such a way as to obtain the formation of the nanocapsules in an aqueous suspension.

The subject of the invention is also nanocapsules which can be obtained according to the method of the invention, in particular nanocapsules comprising an oily core in which an active ingredient is homogeneously dispersed and a polymeric shell formed from a hydrophobic polymer and from a hydrophilic polymer, which can be obtained according to the method of the invention, and also aqueous suspensions of such nanocapsules.

According to another of its aspects, the invention relates to the pharmaceutical, cosmetic or food compositions comprising nanocapsules according to the invention or an aqueous suspension of nanocapsules according to the invention, in combination with at least one pharmaceutically or physiologically acceptable excipient.

Some definitions of terms used in the context of the description of the invention are given hereinafter.

BRIEF DESCRIPTION OF THE DRAWINGS

The sole FIGURE illustrates a microscopic image of the appearance of nanocapsules of chlorhexidene base.

DETAILED DESCRIPTION OF THE INVENTION

The notions of solubility, miscibility and solubilization are well known to those skilled in the art. Reference may in particular be made to Physical Pharmacy ($4^{th}$ edition, Alfred Martin (ed.), Lea & Febiger Philadelphia, London) chapter 10, pp 212-250, chapter 15, pp 393-422. Unless otherwise indicated, in the context of the invention, the solubility, miscibility or solubility is obtained at ambient temperature, in particular at 20° C.

In particular, in the context of the invention, the term "miscible" is intended to mean completely miscible. Two liquid compounds will be considered to be completely miscible when they mix together in any proportion. Consequently, the term "miscibility" refers to the mutual solubility of the compounds in the liquid systems.

In particular, for the purpose of the invention, a solid compound will be considered to be soluble in a liquid or mixture of liquids when this compound disperses homogeneously in the molecular state under the effect of spontaneous solid/liquid interactions. An active ingredient is considered to be soluble in a liquid or mixture of liquids when 1 g of active ingredient is dissolved in 10 to 30 ml of liquid or mixture of liquids (US Pharmacopeia).

Regarding solubilization, a solid or liquid (inorganic or organic) compound will be considered to be solubilized in a liquid or mixture of liquids in particular when an association of colloids forming micelles increases the solubility of the compound initially insoluble in the dispersing medium.

The term "hydrophilic" polymer is intended to mean a polymer which is soluble in water. The term "polymer soluble in an aqueous solution" is intended to mean a polymer which, when introduced into water at 20° C., at a concentration by weight equal to 1%, makes it possible to obtain a solution which has a maximum light transmittance value, at a wavelength at which the polymer does not absorb, through a sample 1 cm thick, of at least 70%, preferably of at least 80%.

The term "hydrophobic" polymer is intended to mean a polymer which is insoluble in water.

The term "oil" is intended to mean a lipophilic fatty substance which is liquid at ambient temperature (20° C.) and which is immiscible with water or weakly miscible with water. The term "water-dispersible" oil is intended to mean an oil which disperses in water in the molecular, colloidal or micrometric state.

The HLB (hydrophilic lipophilic balance) will be determined by the Griffin method. (Griffin WC: Classification of Surface-Active Agents by 'HLB,' Journal of the Society of Cosmetic Chemists 1 (1949): 311. Griffin WC: Calculation of HLB Values of Non-Ionic Surfactants, Journal of the Society of Cosmetic Chemists 5 (1954): 259).

The diameter of the nanocapsules, which corresponds to the largest dimension of the nanocapsules, will be determined by photon correlation spectroscopy.

The term "hydrogel" is intended to mean a gelatinous homogeneous mixture forming a single phase containing water, and preferably comprising at least 0.1% to 5% by mass, preferably 0.15% to 2% by mass, of water.

The method according to the invention makes it possible to obtain an aqueous suspension of nanocapsules by means of a gelling emulsion method which does not involve any organic solvent.

As a result, the novel method for preparing an aqueous suspension of nanocapsules according to the invention stands out from the other techniques previously described:

by virtue of the absence of organic solvents used to dissolve the hydrophobic polymers before dispersion of the organic mixture in the polar phase;

by virtue of the absence of a procedure for evaporation or dialysis of organic solvents after nanocapsule formation;

by virtue of the production of a suspension of nanocapsules which is compatible with an invasive or noninvasive administration.

The hydrophilic polymer present within the polymeric shell makes it possible to reduce the interfacial tension existing between the hydrophobic polymer and the water, and thus increases the stability of the suspension obtained. It is thus possible to spontaneously obtain the formation of nanocapsules during the mixing of the two phases, without the use of a volatile organic solvent, as was the case in the prior techniques.

In the context of the invention, two phases, called oily phase and polar phase, are mixed so as to result in the spontaneous formation of nanocapsules. The percentages given below correspond:

with regard to the oily phase, to the percentage by mass of each component relative to the total mass of the oily phase, with regard to the polar phase, to the percentage by mass of each component relative to the total mass of the polar phase.

The oily phase comprises a hydrophobic polymer, an oil, or a mixture of oils, at least one active ingredient, and a surfactant $TA_1$. This oily phase is homogeneous.

The oil(s) used is (are) by nature hydrophobic and can, in certain cases, be water-dispersible. This oil or mixture of oils is intended to form the core of the nanocapsules.

In particular the oil or the mixture of oils can have an HLB included in the range of from 3 to 6.

By way of example of an oil which can be used in the context of the invention, mention may be made of triglycerides, in particular medium-chain triglycerides, propylene glycol dicaprylocaprate, and oleoyl, lauroyl and linoleoyl macrogolglycerides.

The oily phase advantageously comprises from 5% to 20% by mass, preferably from 8% to 12% by mass, of oil or mixture of oils. Of course, this percentage relates only to the oil or mixture of oils and especially does not comprise the active ingredient and/or the surfactant $TA_1$, even when the latter are also in an oily form.

The oily phase contains a hydrophobic polymer in the molten state, the oily phase being maintained at a temperature $T_1$ higher than the melting point of the polymer. The hydrophobic polymer will be chosen in such a way that its melting point is compatible with the physiochemical stability of the oil, of the active ingredient and of the surfactant $TA_1$. In particular, the hydrophobic polymer will have a melting point of preferably lower than or equal to 120° C. In particular, the hydrophobic polymer can be chosen from vinyl polymers, polyesters, polyamides, polyurethanes and polycarbonates, preferably having a melting point lower than 120° C., such as poly-$\epsilon$-caprolactones. The oily phase can in particular comprise from 5% to 20% by mass, preferably from 8% to 12% by mass, of hydrophobic polymer.

The oily phase also contains an active ingredient which is dispersed, in a miscible, soluble or solubilized form, in said oily phase. The active ingredient is miscible, soluble or solubilized in the mixture composed of the surfactant $TA_1$ and of the oil or mixture of oils, at the temperature $T_1$. According to one embodiment variation, the active ingredient is also miscible, soluble or solubilized in the mixture composed of the surfactant $TA_1$ and of the oil or mixture of oils, at ambient temperature, in particular at 20° C. When the active ingredient is solubilized, its solubilization is realised through the action of the surfactant $TA_1$, acting as a solubilizing agent.

By way of example of an active ingredient, mention may be made of chlorhexidine base, minoxidil, albendazole and ketoconazole. For example, the oily phase will comprise from 0.5% to 5% by mass, preferably from 1% to 3% by mass, of active ingredient.

The oily phase also comprises a surfactant $TA_1$, which may in particular act as a solubilizing agent for the active ingredient. This surfactant $TA_1$ may be of the anionic, cationic, amphoteric or nonionic type. In particular, the surfactant $TA_1$ can be in the form of an oil. The surfactant $TA_1$ can have an HLB included in the range of from 3 to 6. By way of example of a surfactant $TA_1$, mention may be made of propylene glycol laurates, propylene glycol caprylates, polyglyceryl oleates and caprylocaproyl macrogolglycerides. According to one embodiment, the oily phase comprises from 55% to 89.5% by mass, preferably from 73% to 83% by mass, of surfactant $TA_1$.

Of course, the oily phase may contain a single or several active ingredients and/or a single or several hydrophobic polymers and/or a single or several surfactants $TA_1$, which meet the above criteria.

The oily phase can, for example, be prepared by heating the hydrophobic polymer to a temperature higher than its melting point, and then adding the oil or the mixture of oils and then the active ingredient. The surfactant $TA_1$ can be introduced at any stage. The mixing can be carried out in an entirely different order or the components as a whole can all be mixed simultaneously. It is also possible to heat the oil or the mixture of oils to the temperature $T_1$ and then to add the hydrophobic polymer in the liquid state, and then the other components. The oily phase obtained will have to be homogeneous, and, if necessary, will be homogenized, for example with mechanical stirring.

The polar phase, for its part, contains, in an aqueous solution, a hydrophilic polymer in the form of a hydrogel and a surfactant $TA_2$.

By way of example, the hydrophilic polymer can be chosen from synthetic cellulosic derivatives, preferably from cellulose ethers, such as methylcellulose, ethylcellulose, hydroxyethylcellulose, hydroxypropylcellulose, hydroxyethylmethylcellulose, hydroxypropylmethylcellulose, methylethylcellulose and sodium carboxymethylcellulose. According to one embodiment, the polar phase comprises from 0.1% to 5% by mass, preferably from 0.15% to 2% by mass, of hydrophilic polymer.

The surfactant $TA_2$ may be of the anionic, cationic, amphoteric or nonionic type. According to one embodiment variation, the surfactant $TA_2$ has an HLB of greater than or equal to 15, and is preferably chosen from neutral surfactants (e.g., polysorbate 20, 60, 80; macrogol stearate; macrogol cetostearyl ether; macrogol lauryl ether; macrogol oleyl ether; macrogol oleate; polyoxyl castor oil; hydrogenated polyoxyl castor oil; source: Eur. Ph.). According to one embodiment, the polar phase comprises from 0.1% to 5% by mass, preferably from 0.2% to 2% by mass, of surfactant $TA_2$.

Of course, the polar phase may contain a single or several hydrophilic polymers and/or a single or several surfactants $TA_2$, which meet the above criteria.

The polar phase comprises, most commonly, from 90% to 99.8% by mass, preferably from 96% to 99.65% by mass, of water or of a mixture of water with one or more polar solvents. By way of example of polar solvents, mention may be made of ethanol, 1-propanol and 2-propanol.

The proportion of polar phase relative to the oily phase is variable. Use may in particular be made of a hydrophobic polymer/hydrophilic polymer mass ratio of less than or equal to 0.4.

The mixing of the oily phase and the polar phase can be carried out in various ways. It is possible to pour the oily phase into the polar phase or to mix the two phases by means of a Y-shaped mixer circuit, each of the two phases being conveyed in one of the two arms of the Y. However, the mixing of the two phases is preferably carried out by adding the polar phase to the oily phase, with stirring. The oily phase is then maintained at the desired temperature $T_1$ during the mixing.

At the time of mixing, the oily phase is at a temperature $T_1$ higher than the melting point of the hydrophobic polymer. A temperature which is 10 to 30° C. higher than the melting point of the hydrophobic polymer will in particular be used. Of course, this temperature will not be too high, so as to avoid any degradation of the other components used in the method according to the invention. At this temperature $T_1$, the mixture composed of the oil or the mixture of oils and of the surfactant $TA_1$ is miscible with the hydrophobic polymer, and the active ingredient is also miscible, soluble or solubilized, optionally by virtue of the surfactant $TA_1$, in the mixture composed of the oil or the mixture of oils and of the surfactant $TA_1$.

At the time of mixing or just before the mixing, the polar phase may be at ambient temperature, in particular at 20° C., or, according to one embodiment variation, the polar phase may also be heated. In particular, the polar phase is brought to a temperature $T_2$ which is 2 to 5° C. lower than the melting point of the hydrophobic polymer. It is nevertheless important to preserve, under the mixing conditions, the hydrogel nature of the hydrophilic polymer.

According to one advantageous arrangement of the invention, the mixing of the two phases is carried out with moderate stirring, preferably using mechanical means operating at a speed included in the range of from 4000 to 16000 rpm, preferably in the range of from 6000 to 8000 rpm. By way of example of an emulsifying device suitable for the method according to the invention, mention may be made of a mechanical propeller stirrer or a homogenizer (Ultra-Turrax®).

The method according to the invention results in nanocapsules having a diameter of less than 1000 nanometers. These nanocapsules are obtained in an aqueous suspension which is in the form of a gelatinous homogeneous mixture. The active ingredient can be encapsulated in the oily core of the nanocapsules, or else can be adsorbed within the polymeric shell. The hydrophilic polymer probably forms a protective colloid around the nanocapsules, ensuring greater stability of the colloidal suspension obtained and an improvement in the emulsification process. The concentration of hydrophilic polymer may be adjusted according to the targeted application and, in particular, in the case of the therapeutic compositions, to the selected method of administration. The gelatinous aqueous suspension of nanocapsules obtained can be diluted in water, without notable modification of the stability of the colloidal suspension. The electric charge carried by the nanocapsules will depend on the nature and on the concentration of the protective colloid which coats or is entangled with the hydrophobic polymer constituting the wall of the nanocapsules. In particular, the nanocapsules obtained have a diameter included in the range of from 200 to 1000 nm, preferably in the range of from 300 to 500 nm. The stability in colloidal suspension of these nanocapsules is established. They confer on the active ingredient which they encapsulate in their core, or which is adsorbed within the polymeric shell, protection during storage and also during their transport to their site of action. These nanoparticles are therefore entirely suitable for use as a colloidal system for delivering active ingredients, in particular pharmaceutical or cosmetic active ingredients.

The nanocapsules according to the invention can be used, in particular, in pharmaceutical, cosmetic or food compositions. In such compositions, the nanocapsules are, in general, present in combination with at least one pharmaceutically or physiologically acceptable excipient or vehicle, in particular an excipient which can be administered to humans and/or applied to the skin or the mucous membranes.

When the compositions according to the invention contain an active ingredient chosen from pharmaceutical or cosmetic active agents, mention may be made, by way of example, of chlorhexidine base, minoxidil, albendazole and ketoconazole. Such compositions according to the invention contain a medium or at least one pharmaceutically or physiologically acceptable excipient. Such compositions may in particular be administered enterally, parenterally or topically.

The example hereinafter, with reference to the attached FIGURE, makes it possible to illustrate the invention but is in no way limiting in nature.

EXAMPLE

The qualitative and quantitative composition of an aqueous suspension of nanocapsules loaded with chlorhexidine base is given below:

| Polycaprolactone (cas #24980-41-4) (PCL) | 375 mg |
| Labrafil ® M 1944 CS (cas #97488-91-0 and cas #9004-96-0) | 360 mg |
| Plurol ® oleique (cas # 9007-48-1) | 4 g |
| Chlorhexidine base (cas #55-56-1) | 90 mg |
| Sodium carboxymethylcellulose (cas #9004-32-4) | 1 g |
| 0.15% solution of Tween ® 80 (cas #9005-65-5) | qs 100 g |

In a first step, the PCL is melted at approximately 65° C. in a beaker. The water-dispersible oils (Labrafil® M 1944 CS and Plurol® oleique) are mixed with the molten PCL, with moderate mechanical stirring using an Ultra-Turrax®. The chlorhexidine base is dispersed with the molten PCL and the water-dispersible oils until a clear mixture is obtained. A hydrogel of carboxymethylcellulose at 1% in distilled water is heated to 60° C. in order to be dispersed, with moderate mechanical stirring using an Ultra-Turrax®, in the molten PCT/water-dispersible oils/chlorhexidine base mixture. The formation of the nanocapsules is spontaneous under the effect of the aggregation of the PCL on contact with the hydrogel. However, the stability of the nanocapsule suspension is maintained through the protective effect of the hydrophilic colloid (i.e., sodium carboxymethylcellulose) against the PCL flocculation phenomena.

The size and the zeta potential of the nanocapsules, determined using a Zetamaster® S, are 450 nm and −40 mV, respectively. The concentration of free (i.e. nonencapsulated) chiorhexidine in the nanocapsule suspension was determined after filtration of the colloidal suspension through a 0.22 μm filter. After dilution in distilled water, the concentration of chlorhexidine base free in the filtrate, determined by high performance liquid chromatography (HPLC) (H. Lboutounne, V. Faivre, F. Faison, and F. Pirot, *Skin Pharmacology and Applied Skin Physiology* 17: 176-182 (2004); H. Lboutounne, J.-F. Chaulet, C. Ploton, F. Faison, and F. Pirot *Journal of Controlled Release* 82: 319-334 (2002); D. T. T. Nhung, A.-M. Freydiere, H. Constant, F. Faison, and F. Pirot *International Journal of Pharmaceutics* 334:166-172 (2007)), was in the region of 0.008%, i.e. the saturation concentration of chiorhexidine base in water. The concentration of encapsulated chlorhexidine base was determined by virtue of the difference between the total concentration of chlorhexidine base in the suspension and the concentration of free chlorhexidine. The total concentration of encapsulated chiorhexidine base was determined after dilution of an aliquot of colloidal suspension in a mixture of acetonitrile/sodium acetate (30 mM) (50/50, v/v). The diluting in this mixture has the effect of dissolving the nanocapsules and releasing the encapsulated chiorhexidine base. The concentration of encapsulated chlorhexidine was 0.082% (percentage by mass/volume), i.e. an encapsulation yield of close to 90%. The appearance of the nanocapsules of chlorhexidine base is given in the single FIGURE which shows the image obtained by microscopic examination (×1000) (Axioskop 50 Microscope, Zeiss).

The invention claimed is:

1. A method for preparing an aqueous suspension of nanocapsules comprising an oily core in which an active ingredient is homogenously dispersed and surrounded by a polymeric shell that is formed from a hydrophobic polymer and from a hydrophilic polymer, wherein the method comprises these successive steps: the following phases are mixed:
   a) a first phase, called an oily phase, comprising:
      the hydrophobic polymer,
      an oil or a mixture of oils,
      at least one active ingredient,
      and a surfactant $TA_1$,
      with the absence of organic solvents used to dissolve the hydrophobic polymer,
      is brought to a temperature $T_1$ higher than the melting point of the hydrophobic polymer, the hydrophobic polymer being miscible, at this temperature $T_1$, with the mixture of the surfactant $TA_1$ and the oil or mixture of oils, and the active ingredient being miscible, soluble or solubilized in the mixture of the surfactant $TA_1$ and the oil or mixture of oils;

b) the first phase of step a) is mixed with a second phase, called a polar phase, comprising the hydrophilic polymer in the form of a hydrogel in an aqueous solution containing a surfactant $TA_2$, in such a way as to obtain the formation of the nanocapsules in an aqueous suspension.

2. The method as claimed in claim 1, characterized in that the mixing of the two phases is carried out by adding the polar phase to the oily phase, with stirring.

3. The method as claimed in claim 1, characterized in that the polar phase is brought to a temperature $T_2$ which is 2 to 5° C. lower than the melting point of the hydrophobic polymer.

4. The method as claimed in claim 1, characterized in that the active ingredient is miscible, soluble or solubilized in the mixture of the surfactant $TA_1$ and the oil or mixture of oils, at ambient temperature, in particular at 20° C.

5. The method as claimed in claim 1, characterized in that the oil or the mixture of oils has an HLB included in the range of from 3 to 6.

6. The method as claimed in claim 1, characterized in that the active ingredient is chosen from pharmaceutical or cosmetic active agents.

7. The method as claimed in claim 1, characterized in that the oil(s) is (are) selected from the group consisting of triglycerides, propylene glycol dicaprylocaprates, and oleoyl, lauroyl and linoleoyl macrogolglycerides.

8. The method as claimed in claim 1, characterized in that the surfactant $TA_1$ has an HLB included in the range of from 3 to 6.

9. The method as claimed in claim 1, characterized in that the hydrophobic polymer is selected from the group consisting of vinyl polymers, polyesters, polyamides, polyurethanes and polycarbonates.

10. The method as claimed in claim 1, characterized in that the hydrophilic polymer is selected from the group consisting of methylcellulose, ethylcellulose, hydroxyethylcellulose, hydroxypropylcellulose, hydroxyethylmethylcellulose, hydroxypropylmethylcellulose, methylethylcellulose and sodium carboxymethylcellulose.

11. The method as claimed in claim 1, characterized in that the surfactant $TA_2$ has an HLB of greater than or equal to 15.

12. The method as claimed in claim 1, characterized in that the oily phase comprises from 5% to 20% by mass of hydrophobic polymer.

13. The method as claimed in claim 1, characterized in that the oily phase advantageously comprises from 5% to 20% by mass of oil or mixture of oils.

14. The method as claimed in claim 1, characterized in that the oily phase comprises from 0.5% to 5% by mass of active ingredient.

15. The method as claimed in claim 1, characterized in that the oily phase comprises from 55% to 89.5% by mass of surfactant $TA_1$.

16. The method as claimed in claim 1, characterized in that the polar phase comprises from 0.1% to 5% by mass of hydrophilic polymer.

17. The method as claimed in claim 1, characterized in that the polar phase comprises from 90% to 99.8% by mass of water or of a water/polar solvents mixture.

18. The method as claimed in claim 1, characterized in that the polar phase comprises from 0.1% to 5% by mass of surfactant $TA_2$.

19. The method as claimed in claim 1, characterized in that the hydrophobic polymer/hydrophilic polymer mass ratio is less than or equal to 0.4.

20. The method as claimed in claim 1, characterized in that the nanocapsules obtained have a diameter included in the range of from 200 to 1000 nm.

* * * * *